United States Patent [19]
Mathur

[11] Patent Number: 6,087,393
[45] Date of Patent: Jul. 11, 2000

[54] STABILIZED VITAMIN C FORMULATIONS

[75] Inventor: Rajiv Mathur, Sewell, N.J.

[73] Assignee: IGEN, Inc., Wilmington, Del.

[21] Appl. No.: 09/329,608

[22] Filed: Jun. 10, 1999

[51] Int. Cl.⁷ .................................................. A61K 31/34
[52] U.S. Cl. ............................................................. 514/474
[58] Field of Search ............................................. 514/474

[56] References Cited

U.S. PATENT DOCUMENTS

| | | | |
|---|---|---|---|
| 5,002,761 | 3/1991 | Mueller et al. | 424/70 |
| 5,035,895 | 7/1991 | Shibusawa et al. | 424/450 |
| 5,140,043 | 8/1992 | Darr et al. | 514/474 |
| 5,552,446 | 9/1996 | Candau et al. | 514/772.4 |
| 5,587,149 | 12/1996 | Punto et al. | 424/50 |
| 5,843,411 | 12/1998 | Hernandez et al. | 424/59 |

FOREIGN PATENT DOCUMENTS

| | | |
|---|---|---|
| 1600826 | 9/1970 | France . |
| 53-127819 | 11/1978 | Japan . |

OTHER PUBLICATIONS

England et al., "The biochemical functions of ascorbic acid," *Ann. Rev. Nutr.*, 6:365–406 (1986).

*Primary Examiner*—Raymond Henley, III
*Attorney, Agent, or Firm*—Lahive & Cockfield, LLP

[57] ABSTRACT

The invention features a method of stabilizing free 1-ascorbic acid from oxidation by dispersing the free 1-ascorbic acid in a mixed glycol carrier and a solution containing the ascorbic acid in the mixed glycol solution. The mixed glycol carrier contains a mixture of at least propylene glycol and butylene glycol, but may contain other glycols such as polyethylene glycol , and stabilizing and solubility assisting agents as well.

18 Claims, No Drawings

STABILIZED VITAMIN C FORMULATIONS

BACKGROUND OF THE INVENTION

For many years, researchers have been investigating methods for stabilizing 1-ascorbic acid (vitamin C), due to its beneficial properties. Indeed, 1-ascorbic acid has many known biological functions, such as the stimulation of collagen synthesis, the strengthening of skin tissue against external attack (UV radiation, pollution), depigmentation, activity against free radicals and the compensation for vitamin E deficiency. Some of these beneficial properties have been reported by England and Seifter in the article "The biochemical functions of ascorbic acid" (Ann. Rev. Nutri. (1986) 6:365–406).

However, due to its alpha-keto lactone structure, ascorbic acid is very sensitive to the influence of environmental parameters such as light, oxygen, and water. An unavoidable degradation of ascorbic acid in solution occurs over time due to its pH and the presence of trace metals.

This problem has been addressed in a variety of ways in the art. In order to reduce or delay the degradation of ascorbic acid in solution, U.S. Pat. No. 5,140,043 recommends stabilization by introducing ascorbic acid into aqueous-alcoholic solutions, formed of at least 80% water and having a pH below 3.5. These solutions are not usable in the cosmetic and/or pharmaceutical field because of a combination of pH, drying of the skin by the alcohol, and a lack of aesthetic "feel." Indeed, repeated application of these solutions may disrupt the equilibrium of the skin and may in particular irritate, or even burn, the skin.

Others have tried different ways to produce a stable ascorbic acid solution. B. R. Hajratwala, in "Stability of ascorbic acid", published in the Revue Sciences Pharmaceutiques on Mar. 15, 1905, discloses that ascorbic acid may be stabilized as an acidic aqueous solution by adding an oxyethylenated sorbitan ester surface-active agent. In particular, Hajratwala states that at pH3.4 and 25° C., the addition of this agent reduced the rate of oxidation, and thus the rate of degradation, of ascorbic acid in solution. Hajratwala also discloses the use of a chelating agent such as ethylenediaminetetraacetic acid (EDTA) and packaging under nitrogen, in the absence of light, in order to enhance the stability of the aqueous ascorbic acid solution. However, such an acidic aqueous solution, applied to the skin, has the same drawbacks as those described above for acidic aqueous-alcoholic solutions. Furthermore, the stabilization obtained is still insufficient. Other ways of stabilizing ascorbic acid have been proposed, in particular by a coating technique (FR-A-1,600,826) or by granulation of ascorbic acid (JP-A-53-127,819) for the agri-foods industry.

These techniques, while providing some stability, are, on the one hand, expensive and may, on the other hand, damage the ascorbic acid, for example during heating. Generally, these techniques lead to compositions of poor cosmetic acceptability, as in the case of granules. Consequently, none of the previous proposals have made it possible to overcome the technical problem associated with the instability of ascorbic acid in solution, in a form which is suitable for the cosmetic and/or dermatological fields and at a cost which is compatible with industrial requirements.

Accordingly, an object of the invention is to provide a method and formulation containing ascorbic acid that has improved stability.

Another object of the invention is to provide a method and formulation containing ascorbic acid that has proper aesthetic qualities for use in a dermatological or cosmetic product.

A further object of the invention is to provide a method and formulation containing ascorbic acid that is relatively inexpensive while providing the desire stability and aesthetic properties.

These and other objects and features of the invention will be apparent from the detailed description and the claims.

SUMMARY OF THE INVENTION

The invention pertains, at least in part, to a method of stabilizing free 1-ascorbic acid from oxidation by dispersing the free 1-ascorbic acid in a mixed glycol carrier. This mixed glycol carrier provides both high levels of solubility and stability at a relatively low price. The mixed glycol carrier contains a mixture of at least propylene glycol and butylene glycol, but may contain other glycols such as polyethylene glycol, and stabilizing and solubility assisting agents as well. These additional agents may include diisopropyl adipate, myristyl ether propionate, polyacrylamide (e.g., Sepigel 305), isodecyl neopentonate, diethylene glycol monoethyl ether (e.g., transcutol), lactil (a mixture of sodium lactate, sodium pyrrolidone carboxylic acid, urea, niacinamide, inositol, lactic acid, sodium benzoate, and hydrolized animal protein sold by Goldschmidt A. G.), or mixtures thereof.

The invention also features a solution containing free 1-ascorbic acid stabilized from oxidation in the mixed glycol carrier. The mixed glycol carrier contains a mixture of at least propylene glycol and butylene glycol, but may contain other glycols such as polyethylene glycol, and stabilizing and solubility assisting agents as well. These additional agents may include diisopropyl adipate, myristyl ether propionate, Sepigel 305, isodecyl neopentonate, transcutol, lactil, or mixtures thereof. The preferred range of the propylene glycol in the mixed carrier is 25–80% by weight, with the butylene glycol being 5–30% by weight. A mixed glycol solution of this type can provide a stable solution of 5% or even higher levels of ascorbic acid without oxidative degradation. The dispersion may also include a cosmetically, dermatalogically or pharmaceutically acceptable carrier.

DETAILED DESCRIPTION OF THE INVENTION

The invention features a method of stabilizing free 1-ascorbic acid from oxidation by dispersing the free 1-ascorbic acid in a mixed glycol carrier and a solution containing the ascorbic acid in the mixed glycol solution The mixed glycol carrier contains a mixture of at least propylene glycol and butylene glycol, but may contain other glycols such as polyethylene glycol, and stabilizing and solubility assisting agents as well. These additional agents may include diisopropyl adipate, myristyl ether propionate, polyacrylamide, isodecyl neopentonate, diethylene glycol monoethyl ether, lactil, or mixtures thereof. The preferred range of the propylene glycol in the mixed carrier is 25–80% by weight, with the butylene glycol being 5–30% by weight. A mixed glycol solution of this type can provide a stable solution of 5% or even higher levels of ascorbic acid without oxidative degradation.

The following, non-limiting examples help in illustrating the invention.

EXEMPLIFICATION OF THE INVENTION

Example 1

In this example, solutions were made which incorporated 1-ascorbic acid. This study was performed to test the relative feasibility of incorporating stabilized free 1-ascorbic acid into a solution. The initial solution was made according to the Formulation given in Table 1.

TABLE 1

| Compound | Weight of components in grams |
|---|---|
| L-Ascorbic Acid | 5.0 |
| Propylene Glycol | 94.0 |
| Sepigel 305 | 1.0 |

The 1-ascorbic acid was obtained from Sigma. The propylene glycol was obtained fromOlin Chemicals. Sepigel 305 consists of polyacrylamide, $C_{13}C_{14}$ isoparaffin and laureth-7. An overhead mixer was used to combine the Sepigel and the propylene glycol. The mixture was then heated to approximately 50° C. and stirred 3 hours to disperse the Sepigel. The 1-ascorbic acid was then added and the mixture was is stirred for 30 minutes. The resulting mixture had a pH of 2.97. However, this solution did not provide the stability or aesthetics required for a cosmetic product.

Example 2

In this experiment, the solution was altered to increase he stability and improve the aesthetics of the product. The same procedure referenced above was used to make these solutions. The formulations of these solutions of this example are given in Table 2.

TABLE 2

| | Weight of components in grams | | | |
|---|---|---|---|---|
| Compound | A | B | C | D |
| Polyethylene Glycol | — | — | 10.0 | — |
| Butylene Glycol | 44.5 | 40 | 40.0 | 46.0 |
| Propylene Glycol | 44.5 | 35 | 30.0 | 35.0 |
| Diisopropyl Adipate (Ceraphyl-230) | 5.0 | 10 | 10.0 | 10.0 |
| Myristyl Ether Propionate | — | 5.0 | — | — |
| Sepigel 305 | 1.0 | 1.0 | 1.0 | 1.0 |
| 1-ascorbic acid | 5.0 | 5.0 | 5.0 | 5.0 |

Each solution was made by initially mixing Sepigel 305 with the propylene glycol at 55–60° C. until the solution became clear. The remaining compounds were subsequently added and each solution was then stirred. After prolonged stirring, the resulting solution was uniformly hazy, except for 'A.' 'A' was clear with a good viscosity. After adding the butylene glycol (specifically 1,3 butylene glycol, a material often used in cosmetics)and PEG-200, however, the viscosity of the each solution decreased. After adding all the ingredients, 'D' solution was determined to be superior aesthetically. The non-glycol components are primarily stabilizing elements and can be replaced with similar polymer components.

Example 3

In order to improve the 'feel' and clarity of the solution, the formulations outlined in Table 3 were attempted. The solutions were made in the same method as outlined in Example 2.

TABLE 3

| | Weight of components in grams | | |
|---|---|---|---|
| Compound | A | B | C |
| Butylene Glycol | 35 | 20 | 10 |
| Propylene Glycol | 39 | 44 | 60 |
| Diisopropyl Adipate (Ceraphyl-230) | 20 | 20 | 15 |
| Sepigel 305 | 1.0 | 1.0 | 1.0 |
| 1-ascorbic acid | 5.0 | 5.0 | 5.0 |

The propylene glycol was heated to 55–60° C. and the Sepigel 305 was subsequently added. The solution was then stirred by an overhead mixer until it was clear. The remaining components of the solutions were then added and stirred without additional heating. All of the resulting solutions were hazy. To 'A,' 1.5% Polysorbate 80 was added unsuccessfully to improve the clarity of the solutions. 'C' was the least hazy.

Example 4

In order improve the clarity, the solutions of the formulations outlined in Table 4 were made. The propylene glycol solution was a 1% solution of Sepigel 305 in propylene glycol.

TABLE 4

| | Weight of components in grams | | | | |
|---|---|---|---|---|---|
| Compound | A | B | C | D | E |
| Propylene Glycol Solution | 75 | 85 | 80 | 70 | 80 |
| Butylene Glycol | — | — | 10 | 10 | |
| Diisopropyl Adipate (Ceraphyl-230) | 20 | — | 10 | 10 | |
| Myristyl Ether Propionate (PPG-2) | — | 10 | — | | |
| Isodecyl Neopentonate (DUB ICI) | — | — | — | | 10 |
| 1-ascorbic acid | 5 | 5 | 5 | 5 | 5 |

The solutions were made by adding the remaining components to the propylene glycol solution. All of the resulting solutions were somewhat hazy. In mixtures 'B' and 'E,' the ester components separated out from the other components of the solution. When heated to 50° C., the solutions remained the same. Mixture 'D' had the lightest "feel." It is clear that the combination of propylene glycol and butylene glycol provides advantageous results compared to the solutions lacking the butylene glycol.

Example 5

In the following experiment, transcutol (diethylene glycolmonoethyl ether) was incorporated into the solution mixture. The propylene glycol solution was the same as in Example 4. The formulations of the solutions are outlined in Table 5.

TABLE 5

| | Weight of components in grams | |
|---|---|---|
| Compound | A | B |
| Propylene Glycol Solution | 65 | 60 |
| Butylene Glycol | 10 | 10 |
| Diisopropyl Adipate (Ceraphyl-230) | 15 | 10 |

TABLE 5-continued

| Compound | Weight of components in grams | |
| --- | --- | --- |
|  | A | B |
| transcutol | — | 10 |
| 1-ascorbic acid | 5.0 | 5.0 |

The propylene glycol solution was mixed with the remaining ingredients, as discussed in the preceding Examples. As solution 'A' cooled to room temperature, it became cloudy. When it was reheated, the mixture became clear. Solution 'B' remained clear throughout cooling and reheating. Accordingly, the addition of transcutol appears to provide some advantage.

Example 6

In the following example, the percentage of Sepigel 305 in the propylene glycol solution was increased to 1.25% to improve the clarity of the solutions. The procedure was identical to the one outlined in the preceding Example. The formulations of the solutions are given in Table 6.

TABLE 6

| Compound | Weight of components in grams | | |
| --- | --- | --- | --- |
|  | A | B | C |
| Propylene Glycol Solution | 65 | 60 | 50 |
| 1,3 Butylene Glycol | 15 | 10 | 20 |
| Diisopropyl Adipate (Ceraphyl-230) | 10 | 10 | 15 |
| 1-ascorbic acid | 5 | 5 | 5 |
| transcutol | 5 | 10 | 5 |

After mixing the remaining components with the propylene glycol solution, 'A' and 'C' were slightly hazy and 'B' was clear. Aesthetically, 'C' had a "light" feel. Both 'A' and 'B' were shiny and light.

Example 7

In this example, additional components were added to the solutions. The formulation of the solutions is outlined in Table 7. The propylene glycol solution contained 1.25% Sepigel 305.

TABLE 7

| Compound | Weight of components in grams | | | |
| --- | --- | --- | --- | --- |
|  | A | B | C | D |
| Propylene Glycol Solution | 70 | 70 | 60 | 60 |
| 1,3 Butylene Glycol | 10 | 10 | 15 | 15 |
| Diisopropyl Adipate (Ceraphyl-230) | 10 | 10 | 15 | 15 |
| DC 344 | — | 5 | — | — |
| Lactil | 5 | — | — | — |
| 1-ascorbic acid | 5.0 | 5.0 | 10 | 5.0 |

The 1-ascorbic acid was placed in the propylene glycol solution and heated to approximately 50° C. The mixture was then stirred for about 10 minutes, or until the acid dissolved. The remaining components were then added.

'A' became hazy after adding lactil. The addition of Span 80 (Sorbitan monooleate) did not clear the solution. 'B' became hazy after the addition of DC 344 (Cyclomethicone). The addition of Span 80 did not clarify solution B either. 'C' and 'D' were clear at elevated temperatures, but they became cloudy once they reached room temperature.

Example 8

In this example, the pH of the solutions was increased by adding triethanolamine, magnesium ascorbyl phosphate, and morpholine. The formulations of the solutions are given in the table below. The propylene glycol solution contain 1.25% Sepigel 305.

TABLE 8

| Compound | Weight of components in grams | |
| --- | --- | --- |
|  | A | B |
| Propylene Glycol Solution | 75 | 65 |
| Butylene Glycol | 10 | 15 |
| Diisopropyl Adipate (Ceraphyl-230) | 10 | 10 |
| transcutol | — | 5 |
| 1-ascorbic acid | 5.0 | 5.0 |

L-ascorbic acid was added to the propylene glycol solution and stirred for fifteen minutes. The remaining components were then added. The pH of both solutions was initially 3.01. After the addition of 1 ml triethanolamine, both solutions became hazy. When morpholine was added to another sample, both solutions became hazy. Both sodium hydroxide and magnesium ascorbyl phosphate were not soluble in the solutions.

At room temperature, both 'A' and 'B' remained clear for seven months. At 40° C., both 'A' and 'B' started to yellow after about four months. At 50° C., both samples turned yellow after less than a month.

To yet another sample of 'A,' an additional 5% of 1-ascorbic acid was added. After being warmed slightly and stirred for fifteen minutes, the solution became clear. The pH of the solution was 2.86. At 50° C., 40° C., and room temperature, 'A' was clear. When chilled in the refrigerator, 'A' became hazy. After one month at room temperature, the samples were slightly yellowish. At 50° C. after one month, 'A' was very discolored.

To a sample of 'B,' an additional 5% of 1-ascorbic acid was added at 50° C. The solution remained clear at 50° C., 40° C., and at room temperature. When chilled, 'B' became cloudy. After one month at room temperature, the samples were slightly yellowish. At 50° C. after one month, 'B' was very discolored.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A method of stabilizing free 1-ascorbic acid from oxidation by dispersing said free 1-ascorbic acid in a mixed glycol carrier, said mixed glycerol carrier comprising propylene glycol and butylene glycol, and wherein the dispersion further comprises a stabilizer selected from the group consisting of diisopropyl adipate, myristyl ether propionate, polyacrylamide, isodecyl neopentonate, diethylene glycol monoethyl ether, lactil, and mixtures thereof.

2. The method of claim 1 wherein said mixed glycol carrier comprises 25–80% by weight propylene and 5–30% by weight butylene glycol.

3. The method of claim 1, wherein the dispersion is comprised of about 2% to about 15% free 1-ascorbic acid by weight.

4. The method of claim 1, wherein said mixed glycol carrier further comprises polyethylene glycol.

5. The method of claim 1, wherein said mixed glycol carrier further comprises a cosmetically, dermatalogically or pharmaceutically acceptable carrier.

6. A solution for topical use comprising 1-ascorbic acid in a mixed glycol carrier containing propylene glycol, butylene glycol, and a stabilizer selected from the group consisting of diisopropyl adipate, myristyl ether propionate, polyacrylamide, isodecyl neopentonate, diethylene glycol monoethyl ether, lactil, and mixtures thereof.

7. The solution of claim 6 where said mixed glycol carrier comprises 25–80% by weight propylene glycol and 5–30% by weight butylene glycol.

8. The solution of claim 6 wherein said mixed glycol carrier further comprises polyethylene glycol.

9. The solution of claim 6 wherein said mixed glycol carrier comprises about 75% propylene glycol solution and about 10% butylene glycol, and said solution further comprises about 10% diisopropyl adipate, and about 5% free 1-ascorbic acid.

10. The solution of claim 6 wherein said mixed glycol carrier comprises about 65% propylene glycol solution and about 15% butylene glycol, and said solution further comprises about 10% diisopropyl adipate, about 5% diethylene glycol monoethyl ether, and about 5% free 1-ascorbic acid.

11. The solution of claim 6 wherein said mixed glycol carrier comprises about 60% propylene glycol solution and about 15% 1,3 butylene glycol, and said solution further comprises about 10% diisopropyl adipate, about 10% diethylene glycol monoethyl ether, and about 5% free 1-ascorbic acid.

12. The solution of claim 6 wherein said mixed glycol carrier comprises about 50% propylene glycol solution and about 20% 1,3 butylene glycol, and said solution further comprises about 15% diisopropyl adipate, about 5% diethylene glycol monoethyl ether, and about 5% free 1-ascorbic acid.

13. The solution of claim 6 wherein said mixed glycol carrier comprises about 65% propylene glycol solution and about 10% 1,3 butylene glycol, and said solution further comprises about 15% diisopropyl adipate, and about 5% free 1-ascorbic acid.

14. The solution of claim 6 wherein said mixed glycol carrier comprises about 60% propylene glycol solution and about 10% 1,3 butylene glycol, and said solution further comprises about 10% diisopropyl adipate, about 10% diethylene glycol monoethyl ether, and about 5% free 1-ascorbic acid.

15. The solution of claim 6 wherein said mixed glycol carrier comprises about 70% propylene glycol solution and about 10% butylene glycol, and said solution further comprises about 10% diisopropyl adipate, about 5% lactil and about 5% 1-ascorbic acid.

16. The solution of claim 6 wherein said mixed glycol carrier comprises about 70% propylene glycol solution and about 10% butylene glycol, and said solution further comprises about 10% diisopropyl adipate, about 5% Cyclomethicone and about 5% 1-ascorbic acid.

17. The solution of claim 6 wherein said mixed glycol carrier comprises about 60% propylene glycol solution and about 15% butylene glycol, and said solution further comprises about 15% diisopropyl adipate, and about 10% 1-ascorbic acid.

18. The solution of claim 6 wherein said mixed glycol carrier comprises about 65% propylene glycol solutions and about 15% butylene glycol, and said solution further comprises about 15% diisopropyl adipate, and about 5% 1-ascorbic acid.

\* \* \* \* \*